US008153846B2

(12) United States Patent
Herzog et al.

(10) Patent No.: US 8,153,846 B2
(45) Date of Patent: Apr. 10, 2012

(54) SULFUR CONTAINING FLUOROALKYL AMINES AND ISOCYANATES

(75) Inventors: Axel Hans-Joachim Herzog, West Chester, PA (US); Hollis Thomas Warren, Newark, DE (US); Brent Ryan Gonska, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 111 days.

(21) Appl. No.: 12/273,091

(22) Filed: Nov. 18, 2008

(65) Prior Publication Data
US 2009/0143608 A1 Jun. 4, 2009

Related U.S. Application Data

(60) Provisional application No. 61/005,241, filed on Dec. 3, 2007.

(51) Int. Cl.
C07D 207/27 (2006.01)
C07C 317/28 (2006.01)
(52) U.S. Cl. ........... 564/500; 560/356; 558/15; 548/551
(58) Field of Classification Search .................. 558/61, 558/62, 15; 560/356; 564/500; 548/551
See application file for complete search history.

(56) References Cited

U.S. PATENT DOCUMENTS

| 3,655,732 | A | 4/1972 | Rondestveldt, Jr. |
| 4,126,633 | A | 11/1978 | Toukan et al. |
| 4,171,282 | A | 10/1979 | Mueller |
| 4,490,304 | A | 12/1984 | Falk |
| 4,845,300 | A | 7/1989 | Lantz |
| 4,895,952 | A | 1/1990 | Marty et al. |
| 5,411,766 | A | 5/1995 | Kirchner |
| 5,466,877 | A | 11/1995 | Moore |
| 5,728,887 | A | 3/1998 | Jacobson |
| 6,677,324 | B1 | 1/2004 | Knauthe et al. |

FOREIGN PATENT DOCUMENTS

| DE | 10108543 C | 2/2001 |
| DE | 10332152 | 7/2003 |
| DE | 10332197 | 7/2003 |
| DE | 10332198 | 7/2003 |
| DE | 10332152 | 2/2005 |
| GB | 1231952 A * | 5/1971 |
| JP | 52885127 | 1/1976 |
| JP | 5289633 | 7/1976 |
| JP | 57108063 | 12/1980 |
| WO | WO2005/063842 A1 | 7/2005 |

OTHER PUBLICATIONS

Brighton et al. J. Am. Chem. Soc. 1943, 65, 458-459.*
C. S. Rondestvedt, et al., "Nucleophilic Displacements on beta-(perfluoroalkyl)ethyl iodides. Synthesis of acrylates containing heteroatoms", Journal of Organic Chemistry, Aug. 5, 1977, pp. 2680-2683, vol. 42, No. 16, American Chemical Society, Washington, DC, USA.
Sauer, Dennis Theodore, "Preparation of perfluoroalkylsulfinyl compounds", Univ. Microfilms, Ann Arbor, Mich., Order No. 72-30, 516, Dissertation (1971), 164 pages, Univ. Idaho, Moscow, ID, USA.
Sauer, D. T., et al., "Perfluoroalkylsulfinyl compounds", Journal, 1971, 59, (3-4), 157-62, Dep. Chem., Univ. Idaho, Moscow, ID, USA.

* cited by examiner

Primary Examiner — Joseph Kosack
Assistant Examiner — Matthew P Coughlin
(74) Attorney, Agent, or Firm — Erik W. Perez

(57) ABSTRACT

The present invention provides a method of making sulfur containing fluoroalkyl amines which overcomes the problems of previously known methods. Sulfur containing fluoroalkyl amines are useful as intermediates for compounds which are in turn useful for imparting water and oil repellency to textiles. Sulfur containing fluoroalkyl amines used in this manner may be found in Example 8 of Rondestvedt et al. (U.S. Pat. No. 3,655,732) wherein they are made by reacting an iodo-fluoroalkyl with an aminoalkyl thiol. Specifically, Rondestvedt et al. teaches reacting $CF_3(CF_2)_5(CH_2)_2I$ (an iodo-fluoroalkyl) with $HS-CH_2CH_2-NH_2$ (an aminoalkyl thiol) to make $CF_3(CF_2)_5(CH_2)_2-S-CH_2CH_2-NH_2$ (a sulfur containing fluoroalkyl amine). Unlike previously known methods, the method of the present invention can achieve higher yields of sulfur containing fluoroalkyl amines without resorting to costly solvents. Furthermore, unlike previously known methods, the method of the present invention can produce oxidized forms of sulfur containing fluoroalkyl amines wherein the sulfur atom thereof is oxidized.

7 Claims, No Drawings

SULFUR CONTAINING FLUOROALKYL AMINES AND ISOCYANATES

FIELD OF THE INVENTION

The present invention relates to sulfur containing fluoroalkyl amines, methods for making the same, and isocyanate/isothiocyanate derivatives of the same.

BACKGROUND OF THE INVENTION

Sulfur containing fluoroalkyl amines are useful as intermediates for compounds which are in turn useful for imparting water and oil repellency to textiles. Sulfur containing fluoroalkyl amines used in this manner may be found in Example 8 of Rondestvedt et al. (U.S. Pat. No. 3,655,732) wherein they are made by reacting an iodo-fluoroalkyl with an aminoalkyl thiol. Specifically, Rondestvedt et al. teaches reacting $CF_3(CF_2)_5(CH_2)_2I$ (an iodo-fluoroalkyl) with $HS-CH_2CH_2-NH_2$ (an aminoalkyl thiol) to make $CF_3(CF_2)_5(CH_2)_2-S-CH_2CH_2-NH_2$ (a sulfur containing fluoroalkyl amine).

One disadvantage of preparing sulfur containing fluoroalkyl amines according to the method disclosed by Rondestvedt et al. is that crude product obtained by such a method can contain up to 29 mole percent of impurities. To increase yield and reduce the amount of these impurities, tert-butanol has been used as reaction solvent (*J. Org. Chem.* 1977, 42, 2680-2683); however, tert-butanol is relatively expensive and subsequent isolation of the product can be unpredictably tedious due to foam and emulsion formation.

In addition to problems of poor yield, another disadvantage of preparing sulfur containing fluoroalkyl amines according to the method disclosed by Rondestvedt et al. is that such a method is incapable of producing oxidized forms of sulfur containing fluoroalkyl amines. While Rondestvedt et al. disclose a method of making sulfur containing fluoroalkyl amines such as $CF_3(CF_2)_5(CH_2)_2-S-CH_2CH_2-NH_2$, the method of Rondestvedt et al. cannot produce corresponding oxidized forms such as $CF_3(CF_2)_5(CH_2)_2-S(O)-CH_2CH_2-NH_2$ or $CF_3(CF_2)_5(CH_2)_2-S(O)_2-CH_2CH_2-NH_2$.

BRIEF SUMMARY OF THE INVENTION

The present invention provides a method of making sulfur containing fluoroalkyl amines which overcomes the problems of previously known methods such as the one described by Rondestvedt. For example, unlike previously known methods, the method of the present invention can achieve higher yields of sulfur containing fluoroalkyl amines without resorting to costly solvents. Furthermore, unlike previously known methods, the method of the present invention can produce oxidized forms of sulfur containing fluoroalkyl amines wherein the sulfur atom thereof is oxidized.

In the method of the present invention, a fluoroalkyl thiol is reacted with a N-vinylamide resulting in an amide intermediate which is then subjected to deacylation to make corresponding sulfur containing fluoroalkyl amine. Optionally, the amide intermediate can be subjected to oxidation prior to deacylation thereby producing an oxidized form of sulfur containing fluoroalkyl amines wherein the sulfur atom thereof is oxidized.

Fluoroalkyl thiols useful in the present invention are represented by $R_f$-Q-SH wherein $R_f$ is chosen from a $C_2$-$C_{12}$ perfluoroalkyl provided that: i) one fluorine atom of the perfluoroalkyl can be optionally replaced by hydrogen, and/or ii) the perfluoroalkyl can be optionally interrupted by at least one oxygen, methylene, or ethylene; Q is chosen from the group consisting of a $C_2$-$C_{12}$ hydrocarbylene optionally interrupted by at least one divalent organic group.

N-Vinylamides useful in the present invention are represented by $H_2C=CH-(CH_2)_y-NR-C(O)-R$ wherein y is an integer chosen from 0 to 16, preferably 1, and most preferably 0; and each R is independently chosen from H or a $C_1$ to $C_4$ alkyl, preferably methyl, and most preferably H.

When the aforementioned fluoroalkyl thiols and the aforementioned N-vinylamides are reacted, in accordance with the present invention, the result is an amide intermediate of the present invention represented by $R_f$-Q-S-$C(H)_i(CH_3)_j$-$(CH_2)_{z+(i-1)}$-NR-C(O)-R wherein each R is independently chosen from H or a $C_1$ to $C_4$ alkyl, preferably methyl, and most preferably H; i is 1 or 2, j is 0 or 1; provided that i+j=2. More preferably i=1, j=1, and z=0, Still even more preferably i=2, j=0, and z=0.

Except where otherwise noted, the aforementioned definitions for $R_f$, Q, R, i, j, y and z are applied consistently throughout the specification and claims.

The amide intermediate of the present invention can be subjected to deacylation to produce a sulfur containing fluoroalkyl amine represented by $R_f$-Q-S-$C(H)_i(CH_3)_j$-$(CH_2)_{z+(i-1)}$-NHR wherein R is chosen from H or a $C_1$ to $C_4$ alkyl, preferably methyl, and most preferably H. Optionally, prior to removal of the acyl group, the amide intermediate of the present invention can be subjected to oxidation to produce a sulfur oxide intermediate of the present invention represented by $R_f$-Q-$S(O)_x$-$C(H)_i(CH_3)_j$-$(CH_2)_{z+(i-1)}$-NR-C(O)-R wherein x is 1 or 2. Except where otherwise noted, the aforementioned definition x is used consistently throughout the specification and claims. The sulfur oxide intermediate can then be subjected to deacylation to produce a sulfur containing fluoroalkyl amine of the present invention represented by $R_f$-Q-$S(O)_x$-$C(H)_i(CH_3)_j$-$(CH_2)_{z+(i-1)}$-NHR. Previously known methods were not capable of making sulfur containing fluoroalkyl amines having the -$S(O)_x$- moiety.

Advantageously, the amide intermediate of the present invention of the present invention represented by $R_f$-Q-S-$C(H)_i(CH_3)_j$-$(CH_2)_{z+(i-1)}$-NR-C(O)-R can be subjected to oxidation such that the sulfur atom thereof is selectively oxidized while the amide group, NR-C(O)-R, remains unoxidized. After oxidation, deacylation can be conducted to convert the amide group, NR-C(O)-R, into an amine group, -NHR, thereby resulting in a sulfur containing fluoroalkyl amine wherein the sulfur thereof is oxidized. Previously known methods do not form any intermediate wherein the sulfur atom thereof can be selectively oxidized. In contrast to the present invention, previously known methods only make compounds wherein both a sulfur group, -S-, and an amine group, -NHR, are present thereby rendering the selective oxidation of the sulfur group impossible because of the potential oxidation of the amine group.

DETAILED DESCRIPTION OF THE INVENTION

Unless otherwise stated, the $R_f$ moiety referred to throughout this disclosure is chosen from a $C_2$-$C_{12}$ perfluoroalkyl provided that: i) the perfluoroalkyl can be optionally interrupted by at least one oxygen, methylene, or ethylene; and/or ii) one fluorine atom of the perfluoroalkyl can be optionally substituted by one hydrogen when the perfluoroalkyl is not interrupted by methylene or ethylene. Examples of $R_f$ moieties which are chosen from a perfluoroalkyl without substitutions or interruptions include $(CF_3)_2CF$, and $CF_3(CF_2)_m$ wherein m is an integer from 1 to 11. Examples of $R_f$ moieties which are chosen from a perfluoroalkyl substituted by one hydrogen include $(CF_3)_2CH$, $CF_3(CF_2)_2OCFHCF_2$, and $HC_mF_{2m}$ wherein m is 2 to 12. Examples of $R_f$ moieties which are chosen from a perfluoroalkyl which is interrupted by at least one oxygen include $CF_3(CF_2)_2OCF_2CF_2$ and $CF_3(CF_2)_2OCFHCF_2$, and $CF_3CF_2CF_2[OCF(CF_3)CF_2]_mOCRF$ wherein m is an integer from 6 to 15 and R can be F, $CF_3$, or H. Examples of $R_f$ moieties which are chosen from a $C_2$-$C_{12}$ perfluoroalkyl which is interrupted by at least one methylene include $CF_3(CF_2)_3(CH_2CF_2)_m$ and $CF_3(CF_2)_5(CH_2CF_2)_m$ wherein m is 1, 2, or 3. Examples of $R_f$ moieties which are chosen from a perfluoroalkyl which is interrupted by at least one ethylene include $F[(CF_2CF_2)_n(CH_2CH_2)_m]_kCF_2CF_2$ wherein n=1, 2, or 3 preferably 1; and m=1, or 2 preferably 1; and k=1, 2, or 3.

Unless otherwise stated, the term "fluoroalkyl thiol" or "thiol" as used throughout this disclosure means a compound represented by $R_f$-Q-SH wherein Q is chosen from the group consisting of a $C_2$-$C_{12}$ hydrocarbylene optionally interrupted by at least one divalent organic group. The fluoroalkyl thiols useful in the present invention can be made by any known method. For example, Lantz (U.S. Pat. No. 4,845,300) discloses the following reaction scheme for making thiols useful for the present invention: $R_fCH_2CH_2I+S=C(NH_2)_2 \rightarrow [R_fCH_2CH_2S-(NH_2)_2]^+I^{31}+NaOH \rightarrow R_fCH_2CH_2SH+NaI+O=C(NH_2)_2+MeOH$ wherein $R_f$ is defined therein. Alternatively, Jacobson (U.S. Pat. No. 5,728,887) discloses hydrogenation for making thiols useful for the present invention: $R_fCH_2CH_2SCN+H_2 \rightarrow R_fCH_2CH_2SH+HCN$ wherein $R_f$ is defined therein. Alternatively, a thioacetate intermediate (*J. Fluorine Chem.* 2000, 104, 173-183) can be used according to the following reaction: $R_fCH_2CH_2I+KSOCMe \rightarrow$ (saponification) $\rightarrow R_fCH_2CH_2SH+KOAc$.

Unless otherwise stated, the N-vinylamides referred to throughout this disclosure and useful in the present invention are represented by $H_2C=CH-(CH_2)_y-NR-C(O)-R$ wherein y is an integer chosen from 0 to 16, preferably 1, and most preferably 0; and each R is independently chosen from H or a $C_1$ to $C_4$ alkyl, preferably methyl, and most preferably H. N-Vinylamides useful in the present invention include well known compounds which are commercially available such as N-vinylformamide, N-vinylacetamide, N-vinyl-N-methylacetamide, N-vinylpyrrolidone, and N-allyl formamide.

In the method of the present invention, a fluoroalkyl thiol is reacted with a N-vinylamide resulting in an amide intermediate which is then subjected to deacylation to make a corresponding sulfur containing fluoroalkyl amine. Optionally, the amide intermediate can be subjected to oxidation prior to deacylation thereby producing an oxidized form of sulfur containing fluoroalkyl amines wherein the sulfur atom thereof is oxidized.

Unless otherwise stated, the amide intermediates referred to throughout this disclosure are represented by $R_f$-Q-S-C(H)$_i$(CH$_3$)$_j$-(CH$_2$)$_{z+(i-1)}$-NR-C(O)-R wherein each R is independently chosen from H or a $C_1$ to $C_4$ alkyl, preferably methyl, and most preferably H. The amide intermediates of the present invention are made by reacting a fluoroalkyl thiol, $R_f$-Q-SH, with a N-vinylamide, $H_2C=CH-(CH_2)_y-NR-C(O)-R$.

Specifically, the amide intermediates of the present invention can be made by the free-radical addition of a fluoroalkyl thiol, $R_f$-Q-SH, to a N-vinylamide, $H_2C=CH-(CH_2)_y-NR-C(O)-R$. Reaction conditions for free-radical conditions are well known in the art. An example of a method for conducting free-radical addition involves dissolving one equivalent of a chosen thiol, one equivalent of a chosen N-vinylamide, and an initiator. The solution is then heated to a temperature (typically about 65° C.) which activates the reaction which is stirred until complete consumption of the thiol as determined by gas chromatography-mass spectrometry (GC/MS) monitoring.

Useful initiators for free-radical addition are well known in the art and include: azo compounds, such as azobisisobutyronitrile and azo-2-cyanovaleric acid; hydroperoxides, such as cumene, t-butyl and t-amyl hydroperoxide; dialkyl peroxides, such as di-t-butyl and dicumylperoxide; peroxyesters, such as t-butylperbenzoate and di-t-butylperoxy phthalate; and diacylperoxides, such as benzoyl peroxide and lauryl peroxide; peroxide such as persulfate; and metals such copper. Examples of useful organic solvents for free-radical addition include: ethers, such as tetrahydrofuran, dimethoxyethane, 1,4-dioxane; acetates, such as ethyl acetate, butyl acetate, and isopropyl acetate; alcohols, such as 2-methanol, ethanol, methylpropan-2-ol, isopropanol, 2-methoxyethanol (monoglyme), 2-methoxypropan-2-ol; and ketones, such as acetone, methylisobutyl ketone, and methylethyl ketone, such as N-methyl-2-pyrrolidone, and mixtures thereof. Also hydrocarbon solvents such as toluene are suitable.

As an alternative to free-radical addition, the amide intermediates of the present invention can be made by the Michael addition of a fluoroalkyl thiol, $R_f$-Q-SH, to a N-vinylamide, $H_2C=CH-(CH_2)_y-NR-C(O)-R$, using catalytic amounts of a base, such as tertiary ammonium hydroxide or sodium hydride.

The sulfur oxide intermediates of the present invention are made by the oxidation of an amide intermediate using an oxidizing agent, such as peroxides. The oxidation may optionally include catalysts such as sodium tungstate, phenyl phosphonate, trioctylmethyl ammonium bisulfate, and mixtures thereof. When such catalysts are used during oxidation, the —S(O)$_x$— moiety of the resulting sulfur oxide intermediate is —S(O)$_2$—. One example us the use of such catalyst is in *Tetrahedron* 2005, 61, 8315-8327 and Sato et al. reference [27] therein. When no catalysts are used during oxidation, the —S(O)$_x$— moiety of the resulting sulfur oxide intermediate is —S(O)—. An example of a method for conducting oxidation of an amide intermediate involves adding about one mol equivalent of an oxidizing agent (preferably hydrogen peroxide) to about one mol equivalent of an amide intermediate (optionally in the presence of catalyst) in solvent (preferably an alcohol such as ethanol) at a low temperature (typically about 0° C.) and stirring the mixture while allowing to warm (typically to about 50-60° C.) to activate the oxidation reaction. The progress of the reaction can be monitored via gas chromatography. Upon complete conversion (about 5 hours) any excess oxidizing agent is destroyed; for example hydrogen peroxide can be destroyed with a solution of sodium sulfite. The solvent can then be removed by distillation and the resulting residue containing crude product can be washed (e.g. with water) and dried in vacuum.

The sulfur containing fluoroalkyl amines of the present invention can be made by deacylation of an amide intermediate or a sulfur oxide intermediate. Deacylation of an amide intermediate can be performed by acid catalyzed or base catalyzed deacylation. Deacylation of a sulfur oxide intermediate can be performed by acid catalyzed deacylation.

Acid catalyzed deacylation can be conducted by adding to an amide intermediate or a sulfur oxide intermediate in solvent (preferably an alcohol such as ethanol) at a low temperature (typically 0° C.), a molar excess (typically about a six-fold excess) of concentrated acid (e.g. hydrochloric acid). This mixture is stirred and allowed to warm to ambient temperature and after an initial formation of foam the reaction mixture is slowly heated and held at reflux temperature (about 85° C.) for about 5 hours. The progress of the reaction can be monitored via gas chromatography. Upon complete conversion, the pH of the solution is brought to about 8-10 by carefully adding aqueous base (e.g. sodium hydroxide solution). The resulting sulfur containing fluoroalkyl amine in crude form separates as a bottom layer and can be isolated, e.g. with a separatory funnel. Alternatively, if the ammonium salt is desired, no aqueous base is added.

Base catalyzed deacylation can be conducted by adding an excess (typically about a five-fold excess) of concentrated base (e.g. sodium hydroxide) to the amide intermediate in solvent (preferably an alcohol such as ethanol) at a low temperature (typically 0° C.). This mixture is stirred and allowed to warm to ambient temperature and the reaction mixture is slowly heated and held at reflux temperature (about 85° C.) for about 8 hours. The progress of the reaction can be monitored via gas chromatography. The resulting sulfur containing fluoroalkyl amine in crude form separates as a bottom layer and can be isolated, e.g. via a separatory funnel.

One of the advantages of the formation of an amide intermediate of the present invention, $R_f\text{-}Q\text{-}S\text{—}C(H)_i(CH_3)_j\text{—}(CH_2)_{z+(i-1)}\text{—}NR\text{—}C(O)\text{—}R$, is that the sulfur atom therein can be selectively oxidized while the acyl group —C(O)—R is remains unoxidized thereby forming a sulfur oxide intermediate represented by $R_f\text{-}Q\text{-}S(O)_x\text{—}C(H)_i(CH_3)_j\text{—}(CH_2)_{z+(i-1)}\text{—}NR\text{—}C(O)\text{—}R$ wherein x is 1 or 2. The sulfur oxide intermediate can then be subjected to deacylation to convert the amide group, NR—C(O)—R, into an amine group, —NHR, thereby resulting in a sulfur containing fluoroalkyl amine wherein the sulfur thereof is oxidized. Previously known methods do not form any intermediate wherein the sulfur atom thereof can be selectively oxidized. In contrast to the present invention, previously known methods only make compounds wherein both a sulfur group —S— and an amine group —NHR (R is chosen from H or a $C_1$ to $C_4$ alkyl, preferably methyl, and most preferably H) are present thereby rendering the selective oxidation of the sulfur group impossible because of the potential oxidation of the amine group.

Accordingly, it was previously unknown how to make a sulfur containing fluoroalkyl amine of the present invention represented by $R_f\text{-}Q\text{-}S(O)_x\text{—}CH_2\text{—}C(H)_i(CH_3)_j\text{—}(CH_2)_{z+(i-1)}\text{—}NH_2$ wherein:

$R_f$ is chosen from a $C_2$-$C_{12}$ perfluoroalkyl provided that: i) one fluorine atom of the perfluoroalkyl can be optionally replaced by hydrogen, and/or ii) the perfluoroalkyl can be optionally interrupted by at least one oxygen, methylene, or ethylene;

Q is chosen from the group consisting of a $C_2$-$C_{12}$ hydrocarbylene optionally interrupted by at least one divalent organic group; and x is 1 or 2;

z is 0 or 1;

i is 1 or 2, j is 0 or 1; provided that i+j=2.

It was also previously unknown how to make isocyante and isothiocyante derivatives of the sulfur containing fluoroalkyl amine of the present invention, said isocyante and isothiocyante derivatives represented by $R_f\text{-}Q\text{-}S(O)_x\text{—}C(H)_i(CH_3)_j\text{—}(CH_2)_{z+(i-1)}\text{—}N\text{=}C\text{=}X^1$ wherein:

$X^1$ is O or S;

$R_f$ is chosen from a $C_2$-$C_{12}$ perfluoroalkyl provided that: i) one fluorine atom of the perfluoroalkyl can be optionally replaced by hydrogen, and/or ii) the perfluoroalkyl can be optionally interrupted by at least one oxygen, methylene, or ethylene;

Q is chosen from the group consisting of a $C_2$-$C_{12}$ hydrocarbylene optionally interrupted by at least one divalent organic group; and x is 1 or 2;

z is 0 or 1;

i is 1 or 2, j is 0 or 1; provided that i+j=2.

Isocyante and isothiocyante derivatives of the sulfur containing fluoroalkyl amine of the present invention can be made be made by any suitable process which converts a primary amine group (—$NH_2$) to an isocyanate group (—N=C=O) or isothiocyante group (—N=C=S). An example of a method of converting a primary amine group (—$NH_2$) to an isocyanate group (—N=C=O) may be found in Kornek et al. (DE10108543) consistent with the following reaction scheme: $R_f\text{—}CH_2CH_2\text{—}S\text{—}CH_2CH_2\text{—}NH_2 + EtOC(O)Cl + Cl_3SiMe + 2$ $NEt_3 \rightarrow R_f\text{—}CH_2CH_2\text{—}S\text{—}CH_2CH_2\text{—}N\text{=}C\text{=}O + EtOSi(Me)Cl_2 + 2$ $Et_3NHCl$. An example of a method of converting a primary amine group (—$NH_2$) to an isothiocyante group (—N=C=S) may be found in *J. Org. Chem.* 1956, 21, 404-405 consistent with the following reaction scheme: $R_f\text{—}CH_2CH_2\text{—}S\text{—}CH_2CH_2\text{—}NH_2 + CS_2 + EtOC(O)Cl + 2$ $NEt_3 \rightarrow R_f\text{—}CH_2CH_2\text{—}S\text{—}CH_2CH_2\text{—}N\text{=}C\text{=}S + COS + EtOH + 2\ Et_3NHCl$.

EXAMPLES

Table 1 below shows the fluoroalkyl thiols used throughout the examples numbered as Thiol #1, Thiol #2, and Thiol #3. Table 2 below shows amide intermediates made from the thiols in Table 1. Table 3 shows sulfur oxide intermediates made from the amide intermediates of Table 2. Table 4 shows sulfur containing fluorinated amines made from the amide intermediates or sulfur oxide intermediates which are labeled Fluorinated Amine #1, Fluorinated Amine #2, Fluorinated Amine #3, and Fluorinated Amine #4. Table 4 also shows a sulfur containing fluorinated amine salt labeled Fluorinated Amine Salt #1. Table 4 further shows isocyante and isothiocyante derivatives which respectively labeled Fluorinated Isocyanate #1 and Fluorinated Isothiocyanate #1.

TABLE 1

| Thiol | IUPAC Name | Structure |
|---|---|---|
| Thiol #1 | 3,3,4,4,5,5,6,6,7,7,8,8,8-tridecafluoro-octane-1-thiol | $CF_3(CF_2)_5(CH_2)_2SH$ |
| Thiol #2 | 3,3,4,4-tetrafluoro-4-heptafluoropropyloxy-butane-1-thiol | $CF_3(CF_2)_2O(CF_2)_2(CH_2)_2SH$ |
| Thiol #3 | 3,3,5,5,6,6,7,7,8,8,8-undecafluoro-octane-1-thiol | $CF_3(CF_2)_3CH_2CF_2(CH_2)_2SH$ |

TABLE 2

| Amide Intermediate | Structure | Made from this Thiol | Made from this N-vinyl amide |
|---|---|---|---|
| Amide Intermediate #1A | $CF_3(CF_2)_5(CH_2)_2\text{—}S\text{—}CH_2\text{—}CH_2\text{—}NH\text{—}C(O)\text{—}CH_3$ | Thiol #1 | $CH_2\text{=}CH\text{—}NH\text{—}C(O)\text{—}CH_3$ |
| Amide Intermediate #1B(*) | $CF_3(CF_2)_5(CH_2)_2S\text{—}CH_2\text{—}CH_2\text{—}N(CH_3)\text{—}C(O)\text{—}CH_3$ $CF_3(CF_2)_5(CH_2)_2S\text{—}CH(CH_3)\text{—}N(CH_3)\text{—}C(O)\text{—}CH_3$ | Thiol #1 | $CH_2\text{=}CH\text{—}N(CH_3)\text{—}C(O)\text{—}CH_3$ |

TABLE 2-continued

| Amide Intermediate | Structure | Made from this Thiol | Made from this N-vinyl amide |
|---|---|---|---|
| Amide Intermediate #1C | $CF_3(CF_2)_5(CH_2)_2$—S—$CH_2$—$CH_2$—NH—C(O)—H | Thiol #1 | $CH_2$=CH—NH—C(O)—H |
| Amide Intermediate #1D | $CF_3(CF_2)_5(CH_2)_2$—S—$CH_2$—$CH_2$—N (pyrrolidinone ring with O) | Thiol #1 | $H_2C$=CH—N (pyrrolidinone ring with O) |
| Amide Intermediate #2 | $CF_3(CF_2)_2O(CF_2)_2(CH_2)_2$S—$CH_2$—$CH_2$—NH—C(O)—H | Thiol #2 | $CH_2$=CH—NH—C(O)—H |
| Amide Intermediate #3 | $CF_3(CF_2)_3CH_2CF_2(CH_2)_2$S—$CH_2$—$CH_2$—NH—C(O)—H | Thiol #3 | $CH_2$=CH—NH—C(O)—H |

(*)isomeric mixture of N-methyl-N-[2-(3,3,4,4,5,5,6,6,7,7,8,8,8-tridecafluoro-octylsulfanyl)-ethyl]-acetamide and (R,S)-N-methyl-N-[1-(3,3,4,4,5,5,6,6,7,7,8,8,8-tridecafluoro-octylsulfanyl)-ethyl]-acetamide

TABLE 3

| Sulfur oxide intermediate | Structure | Made from oxidation of Amide Intermediate |
|---|---|---|
| Sulfur oxide intermediate #1A | $CF_3(CF_2)_5(CH_2)_2$—S(O)—$CH_2$—$CH_2$—NH—C(O)—H | Amide Intermediate #1C |
| Sulfur oxide intermediate #1B | $CF_3(CF_2)_5(CH_2)_2$—S(O)$_2$—$CH_2$—$CH_2$—NH—C(O)—H | Amide Intermediate #1C |

TABLE 4

| Ex. | Product | Structure | Intermediate used to make product |
|---|---|---|---|
| 1 | Fluorinated Amine #1 | $CF_3(CF_2)_5(CH_2)_2$—S—$CH_2$—$CH_2$—$NH_2$ | Amide Intermediate #1A* |
| 2 | | | Amide Intermediate #1C* |
| 3 | | | Amide Intermediate #1A** |
| 4 | | | Amide Intermediate #1C** |
| 5 | Fluorinated Amine #2 | $CF_3(CF_2)_5(CH_2)_2$—S(O)—$CH_2$—$CH_2$—$NH_2$ | Sulfur oxide intermediate #1A* |
| 6 | Fluorinated Amine #3 | $CF_3(CF_2)_5(CH_2)_2$—S(O)$_2$—$CH_2$—$CH_2$—$NH_2$ | Sulfur oxide intermediate #1B* |
| 7 | Fluorinated Amine #4 | $CF_3(CF_2)_2O(CF_2)_2(CH_2)_2$S—$CH_2$—$CH_2$—$NH_2$ | Amide Intermediate #2* |
| 8 | Fluorinated Amine Salt #1 | $[CF_3(CF_2)_3CH_2CF_2(CH_2)_2$S—$CH_2$—$CH_2$—$NH_3^+]Cl^-$ | Amide Intermediate #3 |
| 9 | Fluorinated Isocyanate #1 | $CF_3(CF_2)_5(CH_2)_2$—S—$CH_2$—$CH_2$—N=C=O | Fluorinated Amine #1 |
| 10 | Fluorinated Isothiocyanate #1 | $CF_3(CF_2)_5(CH_2)_2$—S—$CH_2$—$CH_2$—N=C=S | Fluorinated Amine #1 |

*made by procedure for acid catalyzed deacylation
**made by procedure for base catalyzed deacylation Thiol #1

Thiol #1 was 3,3,4,4,5,5,6,6,7,7,8,8-tridecafluoro-octane-1-thiol which was made as follows. Under nitrogen thiourea (1.1 equivalents) and 1-iodo-2-perfluorohexylethane (1 equivalent) were added to a degassed mixture of dimethoxyethane (DME, 9 parts) and water (1 part). The reaction mixture was held at reflux temperature for 8 hours. Most of the DME was distilled off and the distillation residue was allowed to cool to ambient temperature. Under stirring a solution of sodium methoxide in methanol (1 molar, 1.1 equivalents) was added to the suspension. Degassed water was added to the mixture. Thiol #1 was collected quantitatively as the fluorous bottom layer.

The spectroscopical data for the product were in agreement with those published elsewhere (J. Fluorine Chem. 1985, 28, 341-355 and J. Fluorine Chem. 1989, 42, 59-68).

Thiol #2

Thiol #2 was 3,3,4,4-tetrafluoro-4-heptafluoropropyloxy-butane-1-thiol which was made as follows. 1,1,1,2,2,3,3-heptafluoro-3-[(1,2,2-trifluoroethenyl)oxy]-propane (available from E. I. du Pont de Nemours and Company as PPVE) was reacted with iodine monochloride and subsequently treated with boron trifluoride to furnish 1,1,1,2,2,3,3-heptafluoro-3-[(1-iodo-1,1,2,2-trifluoroethenyl)oxy]-propane (U.S. Pat. No. 5,481,028A). 1,1,1,2,2,3,3-Heptafluoro-3-[(1-iodo-1,1,2,2-trifluoroethenyl)oxy]-propane was then reacted with ethylene in the presence of a peroxide initiator to yield 1,1,2,2-tetrafluoro-1-(1,1,2,2,3,3,3-heptafluoropropyloxy)-4-iodo-butane (US20080113199A1). Under nitrogen, thiourea (1.1 equivalents) and 1,1,2,2-tetrafluoro-1-(1,1,2,2,3,3,3-heptafluoropropyloxy)-4-iodo-butane were added to degassed 1,4-dioxane. The reaction mixture was heated at reflux temperature for 8 hours. The dioxane was distilled off and the distillation residue was allowed to cool to ambient temperature. Under stirring, a thoroughly degassed solution of sodium hydroxide in methanol and water 1:1 (1 molar, 1.1 equivalents) was added to the suspension. The mixture was heated at 50-60° C. for 5 hours. Additional degassed water was added to the mixture. Thiol #2 was collected quantitatively as the fluorous bottom layer and purified via distillation. NMR of Thiol #2 was obtained as follows.

$^1$H-NMR (CDCl$_3$): 1.60 (t, J=17 Hz, 1H, SH), 2.45 (m, 2H, CF$_2$CH$_2$), 2.86 (m, 2H, CH$_2$S).

Thiol #3

Thiol #3 was 3,3,5,5,6,6,7,7,8,8,8-undecafluoro-octane-1-thiol which was made as follows. Under nitrogen, potassium thioacetate (1.1 equivalents) was added to a solution of 1,1,1,2,2,3,3,4,4,6,6-undecafluoro-8-iodo-octane (1 equivalent) in THF. The reaction mixture was stirred at 50° for 5 hours. The THF was removed under reduced pressure. The distillation residue was dissolved in methanol (25 mL/0.1 mol) and treated with hydrochloric acid (37 w/% in water, three fold excess). Additional degassed water was added to the mixture.

Thiol #3 was collected as the fluorous bottom layer and purified via distillation. NMR of Thiol #3 was obtained as follows.

$^1$H-NMR (CDCl$_3$): 1.55 (s, br, 1H, SH), 2.32 (m, 2H, CF$_2$CH$_2$), 2.74 (m, 4H, CH$_2$S and CF$_2$CH$_2$CF$_2$).

Table 1

The following table shows the thiols that were made above.

Thiol #1

Procedure for Amide Intermediate Synthesis

When amide intermediate synthesis was used to make a chosen amide intermediate in the examples below, amide intermediate synthesis was conducted in the following manner. All amide intermediates in the examples were made according to the following procedure. A solution of one equivalent of a chosen thiol, one equivalent of a chosen N-vinylamide, and 0.04 parts (mol equivalents) VAZO 64 (available from E. I. du Pont de Nemours and Company of Wilmington, Del., USA) in inhibitor-free tetrahydrofuran (THF) was slowly warmed to 65° C. At about 45° C. an exotherm occurred, increasing the reaction temperature briefly to 70° C. The reaction was stirred at 65° C. until complete consumption of the thiol was indicated as determined by gas chromatography-mass spectrometry (GC/MS) monitoring for 5 hours.

Amide Intermediate #1A

Amide Intermediate #1A was N-[2-(3,3,4,4,5,5,6,6,7,7,8,8,8-tridecafluoro-octylsulfanyl)-ethyl]-acetamide which was made using amide intermediate synthesis wherein Thiol #1 was the chosen thiol and N-vinylacetamide was the chosen N-vinylamide. All volatiles were removed under reduced pressure to furnish the desired crude amide free of its regioisomer as a light orange oil. NMR of Amide Intermediate #1A was obtained as follows.

$^1$H-NMR (CDCl$_3$): 1.98 (s, 3H, COCH$_3$), 2.36 (m, 2H, CF$_2$CH$_2$), 2.70 (m, 4H, CH$_2$SCH$_2$), 3.43 (m, 2H, CH$_2$N), 5.98 (s, br, 1H, NH).

Amide Intermediate #1B

Amide Intermediate #1B was an isomer mixture of N-methyl-N-[2-(3,3,4,4,5,5,6,6,7,7,8,8,8-tridecafluoro-octylsulfanyl)-ethyl]-acetamide (I) and (R,S)—N-methyl-N-[1-(3,3,4,4,5,5,6,6,7,7,8,8,8-tridecafluoro-octylsulfanyl)-ethyl]-acetamide (II) which was made using amide intermediate synthesis wherein Thiol #1 was the chosen thiol and N-vinyl-N-methyl-acetamide was the chosen N-vinylamide. All volatiles were removed under reduced pressure to furnish crude Amide Intermediate #1B as a mixture of regioisomers of I and II (3:2) as a light orange oil. The crude Amide Intermediate #1B was about 99% pure and was suitable for further use without further purification. The isomers were not separated. NMR of Amide Intermediate #1B was obtained as follows.

$^1$H-NMR (CDCl$_3$): (I): 1.98 (s, 3H, COCH$_3$), 2.35 (m, 2H, CF$_2$CH$_2$), 2.68 (m, 4H, CH$_2$SCH$_2$), 2.96 (s, 3H, NCH$_3$), 3.47 (m, 2H, CH$_2$N); (II): 2.03 (s, 3H, COCH$_3$), 2.35 (m, 2H, CF$_2$CH$_2$), 2.65 (m, 5H, CF$_2$CH$_2$CH$_2$S and CHCH$_3$), 2.80 (s, 3H, NCH$_3$), 3.43 (m, 1H, CHN).

Amide Intermediate #1C

Amide Intermediate #1C was N-[2-(3,3,4,4,5,5,6,6,7,7,8,8,8-tridecafluoro-octylsulfanyl)-ethyl]-formamide which was made using amide intermediate synthesis wherein Thiol #1 was the chosen thiol and N-vinylformamide was the chosen N-vinylamide. All volatiles were removed under reduced pressure to furnish the desired amide as an off-white solid. NMR of Amide Intermediate #1C was obtained as follows.

$^1$H-NMR (CDCl$_3$): 2.33 (m, 2H, CF$_2$CH$_2$), 2.70 (m, 4H, CH$_2$SCH$_2$), 3.39 (m, 1H, 3.42 (m, 2H, CH$_2$N), 6.66 (s, br, 1H, NH), 8.12 (s, 1H, CHO).

Amide Intermediate #1D

Amide Intermediate #1D was 1-[2-(3,3,4,4,5,5,6,6,7,7,8,8,8-tridecafluoro-octylsulfanyl)-ethyl]-pyrrolidin-2-one which was made using amide intermediate synthesis wherein Thiol #1 was the chosen thiol and N-vinylpyrrolidone was the chosen N-vinylamide. All volatiles were removed under reduced pressure to furnish the desired amide as an off-white solid (Mp 64° C.). NMR of Amide Intermediate #1D was obtained as follows.

$^1$H-NMR (CDCl$_3$): 2.02 (m, 2H, CH$_2$CH$_2$CH$_2$), 2.37 (m, 4H, CF$_2$CH$_2$ and CH$_2$C=O), 2.71 (m, 2H, SCH$_2$CH$_2$N), 2.77 (m, 2H, CF$_2$CH$_2$ CH$_2$S), 3.41 (m, 1H, 3.42 (m, 2H, SCH$_2$CH$_2$N), 3.48 (m, 1H, 3.42 (m, 2H, NCH$_2$CH$_2$CH$_2$).

Examples 1-4

In examples 1-4 below, Fluorinated Amine #1 was 2-(3,3,4,4,5,5,6,6,7,7,8,8,8-tridecafluoro-octylsulfanyl)-ethylamine and was made by the deacylation of an amide intermediate as indicated. The NMR obtained in the examples below for Fluorinated Amine #1 is represented as follows.

$^1$H-NMR (CDCl$_3$): 1.28 (br, 2H, NH$_2$), 2.38 (m, 2H, CF$_2$CH$_2$), 2.65 (m, 2H, SCH$_2$), 2.73 (m, 2H, CH$_2$S), 2.89 (m, 2H, CH$_2$N).

$^1$H-NMR (DMSO-d$_6$): 1.46 (br, 2H, NH$_2$), 2.48 (m, 2H, CF$_2$CH$_2$), 2.58 (m, 2H, SCH$_2$), 2.72 (m, 4H, CH$_2$S and CH$_2$N).

$^{13}$C-NMR (CDCl$_3$): 22.3 (s, CH$_2$S), 32.1 (m, CF$_2$CH$_2$), 35.8 (s, SCH$_2$), 40.5 (s, CH$_2$N).

Procedure for Acid Catalyzed Deacylation

When acid catalyzed deacylation was used to make a chosen fluorinated amine in the examples below, acid catalyzed deacylation was conducted in the following manner. Concentrated hydrochloric acid solution (37.5 w/% in water, five to six-fold molar excess) was added to a solution of one equivalent of a chosen amide intermediate in ethanol at 0° C. The reaction mixture was allowed to warm to ambient temperature while being stirred. After the initial foam formation ceased the reaction mixture was slowly heated and held at reflux temperature for 5 hours at about 85° C. The progress of the reaction was monitored via Gas Chromatography. Upon complete conversion, the pH of the solution was brought to 8-10 by carefully adding aqueous sodium hydroxide solution. The chosen fluorinated amine in crude form separated as the bottom layer and was isolated as a brownish slightly viscous liquid via a separatory funnel. The aqueous phase was extracted with diethyl ether. The residue of the dried ether phase was combined with the initial first crop. The chosen fluorinated amine in crude form was washed with water and dried using molecular sieves (4 Å) and was purified by distillation to obtain a colorless liquid in 80 to 95% yield as either a colorless solid or pail yellow liquid.

Example #1

Fluorinated Amine #1 was made by the acid catalyzed deacylation of Amide Intermediate #1A.

Example #2

Fluorinated Amine #1 was made by the acid catalyzed deacylation of Amide Intermediate #1C.

Procedure for Base Catalyzed Deacylation

When base catalyzed deacylation was used to make a chosen fluorinated amine in the examples below, base catalyzed deacylation was conducted in the following manner. An aqueous solution of sodium hydroxide (five equivalents) was added to one equivalent of the chosen fluorinated amine at ambient temperature and the mixture was slowly brought to reflux temperature. After about 8 hours of reaction time, the chosen fluorinated amine in crude form separated as the bottom layer and was isolated as a brownish slightly viscous liquid via a separatory funnel. It was washed with water and dried using molecular sieves (4 Å). The chosen fluorinated amine in crude form was purified by distillation and obtained as a colorless liquid in 80 to 95% yield as either a colorless solid or a pail yellow liquid.

Example #3

Fluorinated Amine #1 was made by the base catalyzed deacylation of Amide Intermediate #1A.

Example #4

Fluorinated Amine #1 was made by the base catalyzed deacylation of Amide Intermediate #1C.
Sulfur Oxide Intermediate #1A Sulfur oxide intermediate #1A was N-[2-(3,3,4,4,5,5,6,6,7,7,8,8,8-tridecafluoro-octane-1-sulfinyl)-ethyl]-formamide which was made by oxidation of Amide Intermediate #1C as follows. Hydrogen peroxide (35 w/% in water, 1.1 mol equivalents) was added to a solution of one equivalent of Amide Intermediate #1C in ethanol at 0° C. The reaction mixture was allowed to warm to ambient temperature while being stirred. The progress of the reaction was monitored via Gas Chromatography. Upon complete conversion (5 hours) any excess peroxide was destroyed by adding a solution of sodium sulfite (negative peroxide test). The ethanol was distilled off; the residue was washed with water and dried in vacuum. The Sulfur oxide intermediate #1 was obtained quantitatively as a colorless solid. Mp 179° C. NMR of Sulfur oxide intermediate #1A was obtained as follows.

$^1$H-NMR (CDCl$_3$): 2.59 (m, 2H, CF$_2$CH$_2$), 2.93 (dm, J=170 Hz, 2H, SOCH$_2$CH$_2$N), 2.96 (m, 2H, CF$_2$CH$_2$CH$_2$SO), 3.84 (m, 2H, CH$_2$N), 6.50 (s, br, 1H, NH), 8.19 (s, 1H, CHO).

$^{13}$C-NMR Spectrum of Sulfur oxide intermediate #1A could not be obtained due to its insufficient solubility most common organic deuterated solvents.
Sulfur Oxide Intermediate #1B Sulfur oxide intermediate #1B was N-[2-(3,3,4,4,5,5,6,6,7,7,8,8,8-tridecafluoro-octane-1-sulfonyl)-ethyl]-formamide which was made by oxidation of Amide Intermediate #1C as follows. A solution of sodium tungstate (0.01 equivalents), phenyl phosphonate (0.01 equivalents), and trioctylmethyl ammonium bisulfate (0.01 equivalents) in hydrogen peroxide (35 w/% in water, 2.2 equivalents) was prepared. This solution was slowly added to a solution of one equivalent of Amide Intermediate #1C in ethanol at 0° C. The reaction mixture was allowed to warm to ambient temperature and then heated to 60° C. while being stirred. The progress of the reaction was monitored via Gas Chromatography. Upon complete conversion any excess peroxide was destroyed by adding a solution of sodium sulfite (negative peroxide test). The ethanol was removed under reduced pressure. The residue was washed with water and dried in vacuum. Sulfur oxide intermediate #1B was obtained quantitatively as a colorless solid. Mp 108° C. NMR of Sulfur oxide intermediate #1B was obtained as follows.

$^1$H-NMR (CDCl$_3$): 2.62 (m, 2H, CF$_2$CH$_2$), 3.28 (m, br, 4H, CH$_2$SO$_2$CH$_2$), 3.83 (m, br, 2H, CH$_2$N), 6.25 (s, br, 1H, NH), 8.19 (s, 1H, CHO).

$^{13}$C-NMR (CDCl$_3$): 22.3 (s, CF$_2$CH$_2$), 33.3 (s, CH$_2$N), 43.4 (s, SO$_2$CH$_2$), 51.6 (s, CH$_2$SO$_2$), 161.7 (s, CHO).

Example 5

Fluorinated Amine #2 was (3,3,4,4,5,5,6,6,7,7,8,8,8-tridecafluoro-octane-1-sulfinyl)-ethylamine which was made by acid catalyzed deacylation of Sulfur oxide intermediate #1A. After acid deacylation, the crude Fluorinated Amine #2 was filtered, washed with water, and dried. The drying step is important because Fluorinated Amine #2 forms adducts with both polar protic and non-protic solvents, respectively. Ethanol was removed from the filtrate under reduced pressure and the residue was washed with water and dried in vacuum. Fluorinated Amine #2 was obtained quantitatively as a colorless solid. Mp>250° C. NMR of Fluorinated Amine #2 was obtained as follows. NMR analysis was performed on crystals obtained from dimethoxyethane (DME) with the following results.

$^1$H-NMR (DMSO-d$_6$): 2.59 (m, 2H, CF$_2$CH$_2$), 2.80 (m, 2H, CH$_2$N), 2.88 (m, 2H, SOCH$_2$), 2.98 (m, 2H, CH$_2$SO).

Example 6

Fluorinated Amine #3 was 2-(3,3,4,4,5,5,6,6,7,7,8,8,8-tridecafluoro-octane-1-sulfonyl)-ethylamine which was made by acid catalyzed deacylation of Sulfur oxide intermediate #1B as follows. Example 5 was duplicated except Sulfur oxide intermediate #1B was used instead of Sulfur oxide intermediate #1A. Fluorinated Amine #3 was obtained quantitatively as a colorless solid, mp>250° C. NMR (in CDCl$_3$) and IR analysis was performed on crystals obtained from dimethoxyethane (DME) with the following results.

$^1$H-NMR (CDCl$_3$): 1.76 (br, 2H, NH$_2$), 2.68 (m, 2H, CF$_2$CH$_2$), 3.14 (m, 2H, CH$_2$N), 3.28 (m, 2H, SO$_2$CH$_2$), 3.39 (m, 2H, CH$_2$SO$_2$), 3.63 (m, 4H, OCH$_3$), 3.75 (m, 4H, OCH$_2$).

$^1$H-NMR (DMSO-d$_6$): 2.71 (m, 2H, CF$_2$CH$_2$), 2.97 (m, 2H, CH$_2$N), 3.27 (m, 2H, SO$_2$CH$_2$), 3.52 (m, 2H, CH$_2$SO$_2$).

$^{13}$C-NMR (CDCl$_3$): 24.5 (s, CF$_2$CH$_2$), 36.2 (m, CH$_2$SO$_2$), 43.1 (s, CH$_2$N), 46.6 (s, SO$_2$CH$_2$), 56.8, 61.9, 71.3, 72.5 (s, DME).

IR Spectrum: 1070 cm−1 (sym. SO2).
Amide Intermediate #2

Amide Intermediate #2 was N-[2-(3,3,4,4-tetrafluoro-4-heptafluoropropyloxy-butylsulfanyl)-ethyl]-formamide was made using amide intermediate synthesis wherein Thiol #2 was the chosen thiol and N-vinylformamide was the chosen N-vinylamide. All volatiles were removed under reduced pressure to furnish the desired crude amide quantitatively with a purity of 97% as an off-white solid. Mp>250° C.

$^1$H-NMR (CDCl$_3$): 2.38 (m, 2H, CF$_2$CH$_2$), 2.77 (m, 4H, CH$_2$SCH$_2$), 3.53 (m, 2H, CH$_2$N), 6.88 (s, br, 1H, NH), 8.20 s, 1H, CHO).

Example 7

Fluorinated Amine #4 was 2-(3,3,4,4-tetrafluoro-4-heptafluoropropyloxy-butylsulfanyl)-ethylamine which was made by acid catalyzed deacylation of Amide Intermediate #2. NMR analysis was performed on crystals obtained from dimethoxyethane (DME) with the following results.

$^1$H-NMR (CDCl$_3$): 1.92 (br, 2H, NH$_2$), 2.32 (m, 2H, CF$_2$CH$_2$), 2.65 (t, 2H, SCH$_2$), 2.73 (m, 2H, CH$_2$S), 2.92 (t, 2H, CH$_2$N).
Amide Intermediate #3

Amide Intermediate #3 was N-[2-(3,3,5,5,6,6,7,7,8,8,8-udecafluoro-octylsulfanyl)-ethyl]-formamide which was made using amide intermediate synthesis wherein Thiol #3 was the chosen thiol and N-vinylformamide was the chosen N-vinylamide. All volatiles were removed under reduced pressure to furnish Amide Intermediate #3 quantitatively with a purity of 97% as an off-white solid. Mp>250° C. NMR of Amide Intermediate #3 was obtained as follows.

$^1$H-NMR (CDCl$_3$): 2.33 (m, 2H, CF$_2$CH$_2$), 2.73 (m, 6H, CH$_2$SCH$_2$ and CF$_2$CH$_2$CF$_2$), 3.54 (m, 2H, CH$_2$N), 6.16 (s, br, 1H, NH), 8.19 (s, 1H, CHO).

Example 8

Fluorinated Amine Salt #1 was 2-(3,3,5,5,6,6,7,7,8,8,8-undecafluoro-octylsulfanyl)-ethyl-ammonium chloride which was made by the deacylation of Amide Intermediate #3 as follows. Concentrated hydrogen chloride solution (37.5 w/% in water, five to six-fold molar excess) was added to a solution of one equivalent of Amide Intermediate #3 in ethanol at 0° C. The reaction mixture was allowed to warm to ambient temperature while being stirred. After the initial foam formation ceased the reaction mixture was stirred at 70° C. for 5 hours. The progress of the reaction was monitored via Gas Chromatography. The Fluorinated Amine Salt #1 was isolated in quantitative yield by stripping all volatiles under reduced pressure.

$^1$H-NMR (MeOH-d4): 2.39 (m, 2H, CF$_2$CH$_2$), 2.81 (m, 4H, CH$_2$S), 2.90 (m, 2H, SCH$_2$), 3.05 (m, 2H, and CF$_2$CH$_2$CF$_2$), 3.19 (m, 2H, CH$_2$N).

Example 9

According to DE10108543(C1), Fluorinated Isocyanate #1 was 1,1,1,2,2,3,3,4,4,5,5,6,6-tridecafluoro-8-(2-isocyanato-ethylsulfanyl)-octane which was made as follows. A solution of one equivalent of Fluorinated Amine #1 (0.1 mol) and one equivalent of triethyl amine (0.1 mol) in dry toluene (350 mL) is cooled to 0° C. (ice bath). Ethyl chloroformate (0.11 mol) is added dropwise within 20 min. The mixture, while stirring, was allowed to warm to room temperature. A second equivalent of triethyl amine (0.1 mol) is added followed by the dropwise addition of methyl trichlorosilane (0.12 mol) at 30-40° C. (addition time about 20-30 min). The mixture was then heated to 100° C. for 1 hour. After the mixture had cooled to ambient temperature the precipitated ammonium salts were filtered off. Under steady N$_2$ flow, both toluene and generated ethoxy methyl dichlorosilane were distilled off at 200 mm Hg. The residue was dried in vacuum to furnish Fluorinated Isocyanate #1 in 95% yield as a light red-brown liquid. NMR analysis yielded the following results.

$^1$H-NMR (CDCl$_3$): 2.34 (m, 2H, CF$_2$CH$_2$), 2.73 (m, 4H, CH$_2$SCH$_2$), 3.45 (m, 2H, CH$_2$N).

$^{13}$C-NMR (CDCl$_3$): 23.1 (s, CH$_2$S), 32.1 (m, CF$_2$CH$_2$), 35.8 (s, SCH$_2$CH$_2$N), 40.5 (s, CH$_2$N), 106-121 (m, CF$_2$), 123.8 (s, NCO).

Example 10

According to *J. Org. Chem.* 1956, 21, 404-405, Fluorinated Isothiocyanate #1 was 1,1,1,2,2,3,3,4,4,5,5,6,6-tridecafluoro-8-(2-isothiocyanato-ethylsulfanyl)-octane which was made as follows. A solution of one equivalent of Fluorinated Amine #1 (0.1 mol) and two equivalents of triethyl amine (0.2 mol) in dry methylene chloride (200 mL) was cooled to 0° C. (ice bath). Carbon disulfide (1.3 equivalents) was added dropwise within 20 min. The mixture was allowed to warm to ambient temperature while stirring was continued for one hour. The reaction mixture was stirred for additional 8 hours at ambient temperature. Toluene (200 mL) was added and precipitated solids were filtered of (Buechner). The solvents of the filtrate were removed in vacuum to furnish the desired product in sufficient purity for further derivatization in 97% yield. NMR analysis yielded the following results.

$^1$H-NMR (CDCl$_3$): 2.35 (m, 2H, CF$_2$CH$_2$), 2.78 (m, 4H, CH$_2$SCH$_2$), 3.68 (m, 2H, CH$_2$N).

$^{13}$C-NMR (CDCl$_3$): 23.1 (s, CH$_2$S), 32.1 (m, CF$_2$CH$_2$), 32.6 (s, SCH$_2$CH$_2$N), 45.0 (s, CH$_2$N), 106-121 (m, CF$_2$), 133.4 (s, NCO).

What is claimed is:

1. A fluoroalkyl amine represented by the formula:

wherein:
  R$_f$ is chosen from:
   a) (CF$_3$)$_2$CF wherein m is an integer from 1 to 11;
   b) (CF$_3$)$_2$CH, CF$_3$(CF$_2$)$_2$OCFHCF$_2$ or HC$_m$F$_{2m}$ wherein m is 2 to 12;
   c) CF$_3$(CF$_2$)$_2$OCF$_2$CF$_2$, CF$_3$(CF$_2$)$_2$OCFHCF$_2$, or CF$_3$CF$_2$CF$_2$[OCF(CF$_3$)CF$_2$]$_m$OCR$^1$F wherein m is an integer from 6 to 15 and R$^1$ is F, CF$_3$, or H;
   d) CF$_3$(CF$_2$)$_5$(CH$_2$CF$_2$)$_m$ wherein m is 1, 2, or 3; and
   e) F[(CF$_2$CF$_2$)$_n$(CH$_2$CH$_2$)$_m$]$_k$CF$_2$CF$_2$ wherein n=1, 2, or 3; m=1, or 2; and k=1, 2, or 3;
  Q is chosen from the group consisting of a C$_2$-C$_{12}$ hydrocarbylene;
  x is 1 or 2;
  z is 0 or 1;
  i is 1 or 2; j is 0 or 1; provided that i+j=2; and
  R is chosen from H and a C$_1$ to C$_4$ alkyl.

2. The fluoroalkyl amine of claim 1 wherein R is H.

3. The fluoroalkyl amine of claim 1 wherein i=1, j=1 and z=0.

4. The fluoroalkyl amine of claim 1 wherein i=2, j=0 and z=0.

5. A fluoroalkyl isocyanate or isothiocyanate represented by the formula:

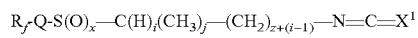

wherein:
  X$^1$ is O or S;
  R$_f$ is chosen from:
   a) (CF$_3$)$_2$CF wherein m is an integer from 1 to 11;
   b) (CF$_3$)$_2$CH, CF$_3$(CF$_2$)$_2$OCFHCF$_2$ or HC$_m$F$_{2m}$ wherein m is 2 to 12;
   c) CF$_3$(CF$_2$)$_2$OCF$_2$CF$_2$, CF$_3$(CF$_2$)$_2$OCFHCF$_2$, or CF$_3$CF$_2$CF$_2$[OCF(CF$_3$)CF$_2$]$_m$OCR$^1$ F wherein m is an integer from 6 to 15 and R$^1$ is F, CF$_3$, or H;
   d) CF$_3$(CF$_2$)$_5$(CH$_2$CF$_2$)$_m$ wherein m is 1, 2, or 3; and
   e) F[(CF$_2$CF$_2$)$_n$(CH$_2$CH$_2$)$_m$]$_k$CF$_2$CF$_2$ wherein n=1, 2, or 3; m=1, 2 or 3; m=1, or 2; and k=1, 2, or 3;
  Q is chosen from the group consisting of a C$_2$-C$_{12}$ hydrocarbylene;
  x is 1 or 2;
  z is 0 or 1; and
  i is 1 or 2; j is 0 or 1; provided that i+j=2.

6. The fluoroalkyl isocyanate or isothiocyanate of claim 5 wherein i=1, j=1 and z=0.

7. The fluoroalkyl isocyanate or isothiocyanate of claim 5 wherein i=2, j=0 and z=0.

* * * * *